United States Patent [19]

Taylor

[11] 4,332,906
[45] Jun. 1, 1982

[54] VESSEL FOR GROWING CELLS
[75] Inventor: Robert L. Taylor, Järfälla, Sweden
[73] Assignee: LKB-Produkter AB, Bromma, Sweden
[21] Appl. No.: 207,025
[22] Filed: Nov. 14, 1980
[30] Foreign Application Priority Data
 Nov. 19, 1979 [SE] Sweden ............................. 79095360
[51] Int. Cl.³ ............................................. C12M 1/34
[52] U.S. Cl. ..................................... 435/291; 422/102
[58] Field of Search ............... 435/284, 285, 286, 289, 435/291, 314, 817; 422/102

[56] References Cited
U.S. PATENT DOCUMENTS
3,660,244  5/1972  Che ..................................... 435/291
4,166,021  8/1979  Ross, Jr. et al. ................. 204/195 F Primary Examiner—Robert J. Warden
Attorney, Agent, or Firm—Fisher, Christen & Sabol

[57] ABSTRACT

A vessel for the growing of cells consists of an outer container provided with a lid which carries an inner container so as to form an annular growing vessel between the containers.

3 Claims, 2 Drawing Figures

VESSEL FOR GROWING CELLS

The present invention refers to a vessel for growing cells, the vessel comprising an outer container provided with a lid in which means for detection of different parameters such as pH, pO$_2$, temperature etc. are suspended along the inner surface of the container.

When growing cells, such as animal- and plant cells, there is often a need of carrying out the growth on a relatively small scale, i.e. in a culture vessel of a small volume. When carrying out the growth process one is however also interested in having access to the possibilities offered by a modern fermenter concerning control of different parameters such as pH, pO$_2$, temperature, CO$_2$ generation, heat flow etc. The commercially available fermenters provided with detection means for measuring and control of these parameters do however have growing vessels the volume of which are relatively large, the smallest having a volume of about one liter, whereas when growing cells the need is often to have a vessel having a volume of some or a couple of hundreds of milliliters.

It is an object of the present invention to provide a vessel for growing cells which can be made relatively small and simultaneously offer the advantages concerning control and monitoring of different parameters which exist in a modern fermenter. The characteristics of the invention will appear from the claims attached to the specification.

Figure 1:
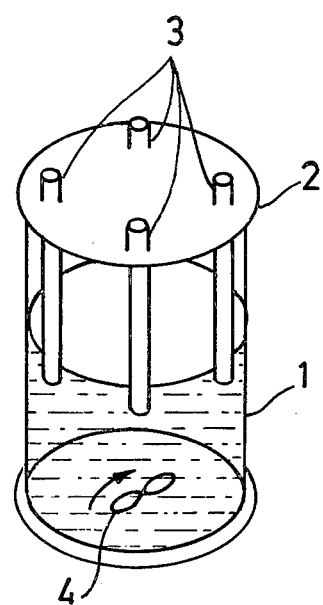

The invention will now be described in detail reference being made to the enclosed drawing in which:

FIG. 1 schematically shows a conventional fermenter; and

Figure 2:
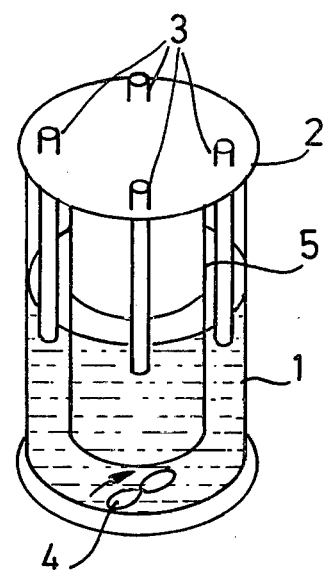

FIG. 2 shows the fermenter according to FIG. 1 modified so as to obtain a vessel according to the invention.

In FIG. 1 reference 1 denotes a cylindrical fermenter vessel provided with a lid 2 on which a number of schematically indicated detecting means 3 are arranged. The fermenter is further provided with a conventional mixing means 4, for instance a magnetic body which is affected by a magnet located outside the fermenter. The means 3 are conventional and are used for detecting and monitoring different parameters being important for the fermentation.

In FIG. 2 there is shown a fermenter according to FIG. 1 modified in such a way that the lid 2 has been provided with an inner container 5 so as to obtain an annular growing vessel between the containers 5 and 1. Thereby a considerably smaller vessel is obtained while maintaining the advantages of a commercial fermenter and thus the growing vessel obtained will be well suited for the growth of cells. The surface of the inner container could also be provided with a membrane through which low molecular side products could pass.

We claim:

1. In apparatus for use with a commercial fermenter vessel of relatively large liquid capacity for the growing of cells in a relatively small volume of liquid culture fluid, said fermenter vessel being of the type wherein the upper margin of the side wall defines a top opening and a removeable closure lid is provided to close said opening, said closure lid including a plurality of downwardly depending detecting and monitoring means arranged adjacent the peripheral margin of the lid, the improvement which comprises an inner compartment secured to the under side of said lid to depend downwardly into said vessel, the outer wall of said container being spaced from the inner wall of said vessel to define an annular chamber for liquid culture fluid into which said detecting and monitoring means depend having a substantially lesser liquid capacity than that of the commercial fermenter vessel itself.

2. Apparatus as defined in claim 1, wherein the bottom wall of said container is spaced above the bottom wall of said vessel, whereby magnetic mixing means may be immersed in the body of liquid culture fluid confined between the walls of said container and vessel.

3. Apparatus as defined in either one of claims 1 or 2, wherein at least a portion of the wall of said container comprises a membrane through which low molecular compounds may pass into the interior of the container.

* * * * *